United States Patent [19]
Kelly

[11] 4,308,861
[45] Jan. 5, 1982

[54] PHARYNGEAL-ESOPHAEGEAL SEGMENT PRESSURE PROSTHESIS
[75] Inventor: Dan H. Kelly, Houston, Tex.
[73] Assignee: Board of Regents, University of Texas, Austin, Tex.
[21] Appl. No.: 134,448
[22] Filed: Mar. 27, 1980
[51] Int. Cl.³ .............................................. A61F 5/00
[52] U.S. Cl. .................................................. 128/68
[58] Field of Search .................. 128/68, 78, 327; 272/94, 85; 403/76, 90, 126, 78, 122, 143

[56] References Cited
U.S. PATENT DOCUMENTS

| 1,793,776 | 2/1931 | Clayton | 128/78 |
| 1,868,891 | 7/1932 | Faudi | 403/122 |
| 2,091,276 | 8/1937 | Gilbert | 128/76 R |
| 2,320,183 | 5/1943 | Jungann | 128/78 |
| 2,617,279 | 11/1952 | Miller, Jr. | 403/122 |
| 3,787,128 | 1/1974 | Maistrelli | 403/122 |
| 4,241,463 | 12/1980 | Khovaylo | 403/143 |

Primary Examiner—Richard C. Pinkham
Assistant Examiner—T. Brown
Attorney, Agent, or Firm—Arnold, White & Durkee

[57] ABSTRACT

A pharyngeal-esophageal segment pressure prosthesis includes a rigid support band having a U-shaped configuration having a pad assembly pivotably and rotatably mounted to its central portion for providing direct pressure to the pharyngeal-esophageal segment area. Connected to the ends of the band is a flexible strap mechanism for securing the device around the neck of the person.

7 Claims, 4 Drawing Figures

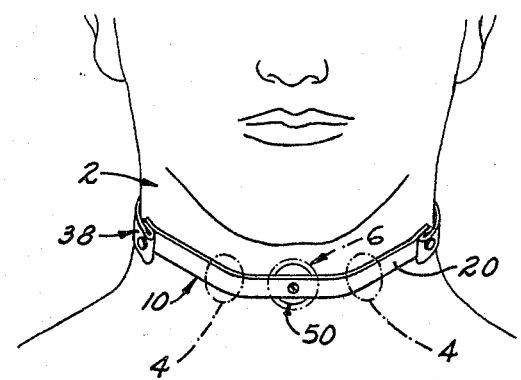
Fig. 1
Fig. 2
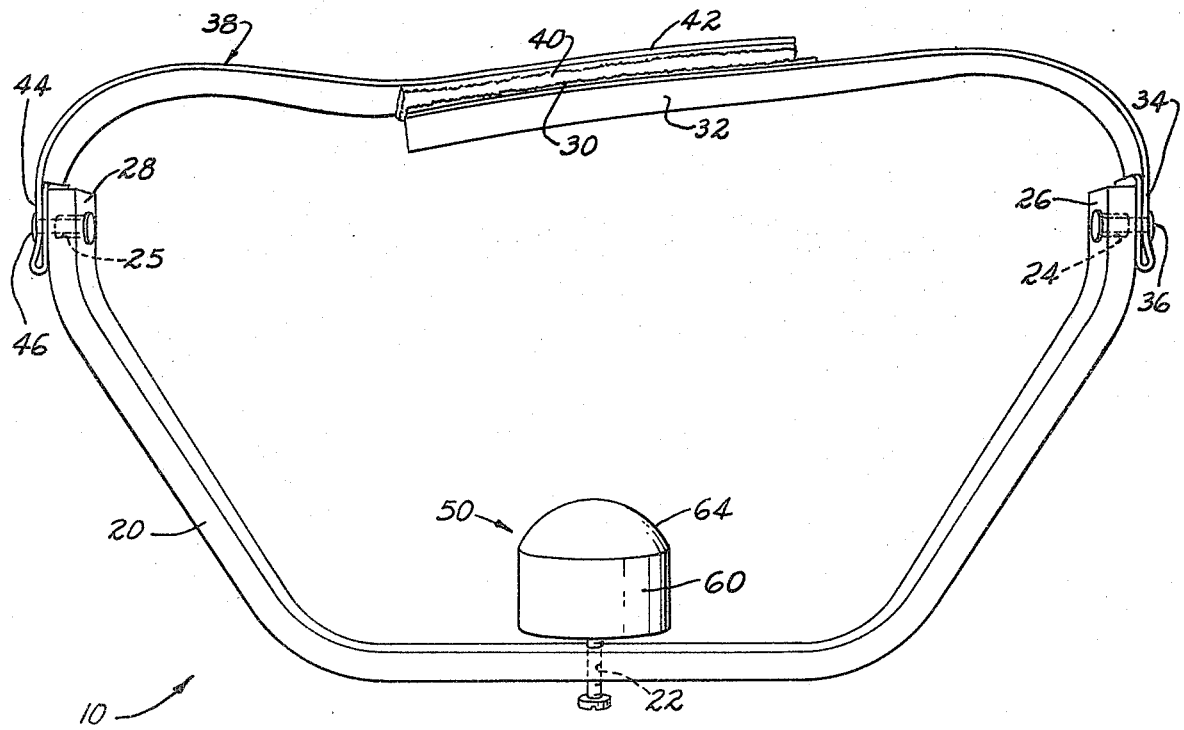

PHARYNGEAL-ESOPHAEGEAL SEGMENT PRESSURE PROSTHESIS

BACKGROUND OF THE INVENTION

1. Field of the Invention

The present invention relates generally to prosthetic devices, and more particularly to a pharyngeal-esophageal segment pressure prosthesis designed to provide direct localized pressure to a weakened pharyngeal-esophageal segment area of a laryngectomized patient.

2. Description of the Prior Art

Each year a number of persons undergo surgical removal of the larynx and associated tissue. In most instances the surgery is required to remove laryngeal carcinoma which is life threatening. Surgical removal of the laryngeal mechanism renders the patient voiceless and speechless.

One of the alternate means of oral communication for the laryngectomized patient is esophageal speech. This technique requires the patient to trap air near the upper end of the esophagus and to release the air in a controlled fashion. As the entrapped air is released the associated walls of the esophagus are set into vibration and sound suitable for voice and speech is produced.

The production of suitable sound from the esophagus is dependent upon the degree of integrity of the pharyngealesophageal segment. Frequently the surgical removal of the larynx and associated tissue reduces the sphincter activity of this segment resulting in the patient's inability to produce suitable esophageal voice for speech.

The problem of a patient presenting a weak pharyngeal-esophageal segment has been addressed a number of different ways by the clinician. The most common technique is to teach the patient to apply digital pressure to the esophagus area, resulting in audible esophageal voice. While oftentimes producing suitable voice, this technique is cumbersome, awkward for the patient and cosmetically unsuitable for most patients. It certainly limits the patient from speaking while engaged in tasks requiring the use of both hands. Other practitioners have used elastic bands to compress the segment area. An elastic band has sometimes been used in conjunction with objects like small balls or molded acrylics placed between the elastic band and the neck of the patient. For a more detailed explanation of the elastic band technique see Grisius, R. J. et al., *Prosthetic Treatment of the Laryngectomized Patient*, 32 J. Prosthet. Dent. 300 (Sept. 1974). The most significant problem with the elastic band technique is the restriction of the flow of blood primarily through the carotid arteries and jugular veins. Additionally, when objects are placed between the elastic band and the neck of the patient they are prone to becoming dislodged and/or displaced with even the slightest amount of movement in the neck area. For example, if the patient wishes to turn or twist the neck area, the elastic band and object arrangement may become dislodged or caused to apply excessive pressure to one area of the neck. The lack of coordinated movement between the prosthesis device and the patient's pharyngeal-esophageal segment area is a major problem in many prior art devices.

As a result of the shortcomings of the prior art, typified by the above, there has developed and continues to exist a substantial need for an inexpensive vocal rehabilitation prosthesis which provides adequate pressure to the pharyngeal-esophageal segment area without restricting cerebral blood flow.

SUMMARY OF THE INVENTION

Therefore as a feature of the present invention a pharyngeal-esophageal segment pressure prosthesis was designed to protect both the carotid arteries and the jugular veins from applied pressure thus overcoming the problem of restricting cerebral blood flow when the device is worn by a patient.

Another feature of the pharyngeal-esophageal segment pressure prosthesis is to provide opportunity to a clinician to provide a device which utilizes a pressure pad best suited for that particular patient by allowing the clinician to selectively interchange pressure pads which attach to the neck support band. In this fashion, a clinician using a single neckband may easily and quickly assess a patient's voice quality and volume by selecting one pressure pad from a set of pressure pads varying in size and shape.

A further feature of this invention is the union ball attachment of the pressure pad to the support band. This feature allows the pressure pad to rock, pivot, or rotate in almost any direction. As a result of this feature, the amount of noise (e.g., klunking or clicking) produced when the patient charges the esophagus with air is reduced. This feature also allows the device to apply a more uniform and constant pressure as the patient rotates or twists the neck area.

A still further feature of this prosthesis is the screw adjustment of the pressure pad. Once the support band is in place and the selected pressure pad in contact with the segment area, pressure on the segment can easily be increased or decreased with the screw adjustment.

Finally the prosthesis is inexpensive, compact, and cosmetically pleasing. It can be worn all day by the patient and does not interfere with breathing or swallowing food taken by mouth.

The present invention is summarized in that a pharyngeal-esophageal segment pressure prosthesis includes a generally U-shaped support band having a pad assembly centrally mounted thereon. The pad assembly includes a pressure pad which presents a curvilinear surface for direct localized contact to a weakened pharyngeal-esophageal segment area. The pad assembly also includes a ball and socket union allowing the pressure pad to freely rotate and pivot. A screw post serves to mount the pressure pad to the support band. Additionally, the screw post may be adjusted to increase or decrease pressure to the segment site. To secure the prosthesis around the neck a strap is coupled to the free ends of the support band.

Other features and advantages of the present invention will become apparent from the following description of a preferred embodiment when taken in conjunction with the accompanying drawings.

BRIEF DESCRIPTION OF THE DRAWINGS

FIG. 1 is a perspective view of a pharyngeal-esophageal segment pressure prosthesis as it is attached around a wearer's neck area;

FIG. 2 is a plan view of the prosthesis shown in FIG. 1;

DETAILED DESCRIPTION OF A PREFERRED EMBODIMENT

Figure 3:
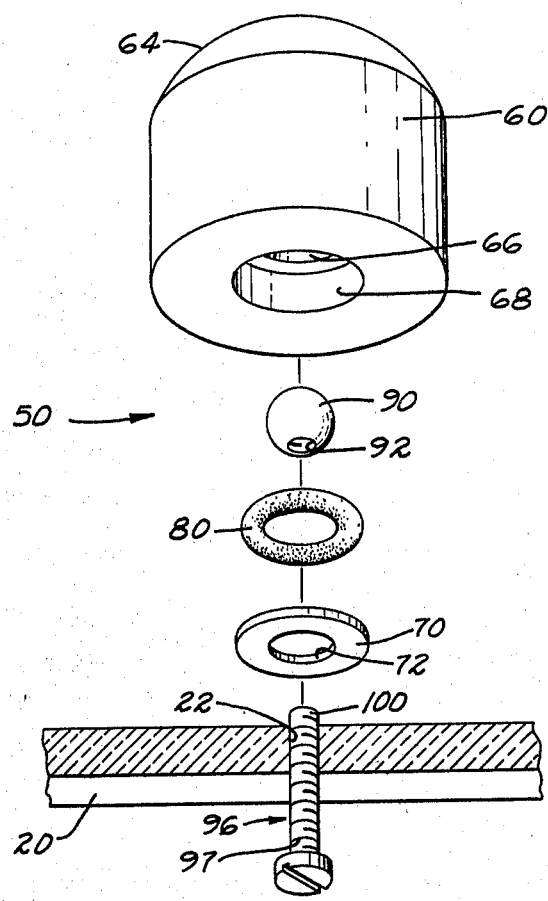
FIG. 3 is an enlarged, exploded, partial plan view of the pad assembly used in the prosthesis of FIG. 1.

Referring to the drawings, and particularly to FIG. 1, there is shown an overall view of a preferred embodiment of a pharyngeal-esophageal segment pressure prosthesis, generally indicated at 10, mounted on the neck area 2 of a post-laryngectomized human patient. In accordance with the present invention, prosthesis 10 includes a rigid support band 20 generally following the frontal contour of the neck 2, a pad assembly 50 centrally mounted on the inner side of the support band 20 between the band 20 and the neck 2 and directly contacting the weakened pharyngeal-esophageal segment area shown generally at 6; and a flexible strap portion 38 coupled to the support band 20 which facilitates securing and removal of the prosthesis 10 around the neck 2. When prosthesis 10 is correctly fitted to a patient's neck so as to permit unrestricted cerebral blood flow, the support band 20 is maintained a spaced distance from the surface of the frontal arch of the neck by the pad assembly 50.

FIG. 2 depicts more specifically the construction of the pharyngeal-esophageal segment pressure prosthesis 10. Support band 20 has generally a U-shaped configuration and may desirably be composed of any rigid material as for example but without limitation a synthetic polymer shaped or molded into an arch generally conforming to the frontal contour of the patient's neck. Further, the width distance between the right inside edge face 26 and the left inside edge face 28 generally corresponds to the maximum width of the wearer's neck.

Prosthesis 10 further includes a flexible strap 38 coupled to the ends of the support band 20. More particularly, the right terminal 34 of strap 38 is folded over and coupled to support band 20 by rivet 36 anchored through hole 24. Similarly, the left terminal 44 of strap 38 is folded over and coupled to the support band 20 by a similar rivet 46 anchored through hole 25. However, as can be understood, the ends of strap 38 may be attached to the band by any of several attachment means such as screws, nut and bolts, etc.

The strap 38 may be constructed of any suitable material such as for example leather, synthetic resins, cloth fibers, and the like. Further, various closure mechanisms may be incorporated into the strap such as the intertwining synthetic fiber means 30 and 40 sewn respectively onto the strap at the closure junctions 32 and 42. This synthetic fiber means 30 and 40 may desirably be a strip of the hook and burr type known as VELCRO. Other closure mechanisms may include clasps, buckles, snaps, hooks and the like.

In accordance with the desired feature of this invention to provide direct localized pressure to a weakened pharyngeal-esophageal segment area 6 (see FIG. 1), prosthesis 10 further comprises a pad assembly 50 mounted to the inner surface of support band 20 through a centrally located bore 22 shown in FIG. 2. Pad assembly 50 directly contacts the pharyngeal-esophageal segment area 6 through pressure pad 60 having a curvilinear surface 64. The size and shape of curvilinear surface 64 may vary according to the needs of the patient in producing the best results.

As can be appreciated from the construction of prosthesis 10 when referring to FIGS. 1 and 2, the properly fitted prosthesis contacts various points along the neck 2 such as the pharyngeal-esophageal segment area 6 by the pressure pad 60; the points of greatest width of the neck by the inner edge faces 26, 28 of the support band 20; and generally the rear portion of the neck back by strap 38. As a result of this construction substantially all the frontal neck area shown generally at areas 4 in FIG. 1 is unconstricted by prosthesis 10 thereby permitting unrestricted blood flow within the neck. In actual use prosthesis 10 may be concealed by an ascot or scarf, if desired for cosmetic reasons.

Referring now to FIG. 3, a detailed view of one embodiment of pad assembly 50 is illustrated. In this view the pad assembly 50 comprises a screw post 96 having a threaded outside surface 97. Screw post 96 is securely attached to the support band 20 by screwing post 96 by means of threads 97 through the centrally located bore 22 which is also threaded to accommodate the threaded outside surface 97 of screw post 96. As can be appreciated from such a construction, the length of screw post 96 which extends inwardly past the inner surface of band 20 may be adjusted by rotating the screw post 96 until the desired length is attained. Further, the second end 100 of screw post 96 is adapted for accepting a ball fitting 90 having a threaded bore 92. Ball fitting 90 serves as a mount for pressure pad 60 by forming the ball portion of a ball and socket joint.

Pressure pad 60 includes a central socket recess 66 (see FIG. 4) having a diameter slightly larger than the diameter of ball fitting 90 which is inset into socket recess 66. It will be appreciated that insertion of ball fitting 90 into socket recess 66 forms a ball and socket joint whereby pressure pad 60 is free to rotate and pivot about the second end 100 of screw post 96.

Figure 4:
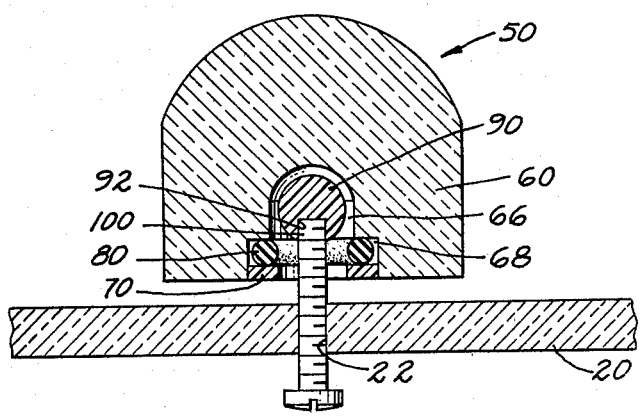
FIG. 4 is an enlarged, partial cross-section of the assembled pad assembly of FIG. 3.

Conjunctively shown in FIGS. 3 and 4, pressure pad 60 may be removably maintained on ball fitting 90 through the use of a retaining assembly comprising a resilient O-ring 80 and a retaining disc 70. Concentric with socket recess 66 a socket collar 68 is counterbored into pressure pad 60. This socket collar 68 has a circumference greater than that of socket recess 66. Collar 68 accommodates the resilient O-ring 80 having an outermost circumference substantially equal to the circumference of socket collar 68. Further, a rigid retaining disc 70 is friction fitted or glued into a recessed position flush with the outer peripheral surface of the pressure pad 50. Ball fitting 90 may then be snap-fitted into socket recess 66 through the retaining disc opening 72 which has a diameter greater than the diameter of ball fitting 90. Moreover ball 90 is pushed through resilient O-ring 80 which has an inside diameter somewhat less than the diameter of ball fitting 90.

Construction of pad assembly 50 in the above described manner allows a person to selectively interchange on the ball fitting any one pressure pad from a set of pressure pads varying in size and shape. Alternatively, the pressure pad 50 may be permanently mounted to the ball fitting 90 by fixing a retaining disc 70 having a disc opening 72 smaller than the circumference of ball fitting 90 but large enough to accommodate screw post 96. Such a disc 70 used to permanently retain the pad 60 is placed on post 96 prior to installation of ball 90 and glued or friction fitted into place in the socket collar 68.

Further modifications and alternative embodiments of the apparatus of this invention will be apparent to those skilled in the art in view of this description. Accordingly, this description is to be construed as illustrative only and is for the purpose of teaching those skilled in the art the manner of carrying out the invention. It is to be understood that the forms of the invention herewith shown and described are to be taken as the presently preferred embodiments. Various changes may be made in the shape, size and arrangement of parts. For example, equivalent elements or materials may be substituted for those illustrated and described herein, parts may be reversed, and certain features of the invention may be utilized independently of the use of other features, all as would be apparent to one skilled in the art after having the benefit of this description of the invention.

What is claimed is:

1. A pharyngeal-esophageal segment pressure prosthesis for providing pressure to a weakened pharyngeal-esophageal segment area of the neck of a laryngectomized person comprising, in combination:
   a rigid support band having substantially a U-shaped configuration;
   a pad assembly having a substantially curvilinear exterior surface for providing diffuse pressure application to the weakened pharyngeal-esophageal segment area of the laryngectomized person, whereby the pressure provided establishes a degree of integrity for the segment area sufficient to permit resonance vibration of the segment area to effect esophageal speech, the pad assembly pivotably and rotatably mounted to the support band; and
   a flexible strap mechanism for securing the prosthesis around the neck, the ends of the strap coupled to the free ends of the support band.

2. The prosthesis of claim 1 wherein the rigid support band has a shape generally conforming to the frontal contour of a neck and has an arch greater than that presented by the frontal arch of the neck.

3. The prosthesis of claim 1 wherein the rigid support band is maintained a spaced distance from the surface of the frontal arch of the neck by the pad assembly whereby the blood flow within the neck is unrestricted by said band.

4. The prosthesis of claim 1 wherein the pad assembly is removably mounted to the support band.

5. The prosthesis of claim 1 wherein the pressure pad assembly further includes a releaseable attachment means connecting said pressure pad to said support band whereby said pressure pad is easily removed.

6. The prosthesis of claim 1 wherein the pad assembly comprises:
   a screw post having its first end rigidly attached to said support band;
   a ball fitting connected to the second end of said screw post;
   a pressure pad having a central socket recess, said ball fitting positioned into said recess, the recess and ball fitting forming a ball and socket joint whereby said pressure pad is free to rotate and pivot about the second end of said screw post; and
   a retaining assembly connected to said pressure pad for maintaining said ball fitting within said socket recess.

7. The prosthesis of claim 1 wherein the pad assembly comprises:
   a screw post having its first end rigidly attached to said support band;
   a ball fitting connected to the second end of said screw post;
   a pressure pad having a central socket recess, said ball fitting positioned into said recess, the recess and ball fitting forming a ball and socket joint whereby said pressure pad is free to rotate and pivot about the second end of said screw post; and a retaining assembly coupled to said pressure pad for removably maintaining said ball fitting within said socket recess.

* * * * *